(12) United States Patent
Gupta et al.

(10) Patent No.: US 8,691,286 B2
(45) Date of Patent: *Apr. 8, 2014

(54) SPUTUM DISSOLVING SUCTIONING SOLUTION FOR ENDOTRACHEAL AND TRACHEOSTOMY TUBES

(75) Inventors: Nisha Gupta, Audobon, PA (US); Erin Peters, Hamburg, PA (US); Joel Rosenblatt, Pottstown, PA (US)

(73) Assignee: Teleflex Medical Incorporated, Durham, NC (US)

( * ) Notice: Subject to any disclaimer, the term of this patent is extended or adjusted under 35 U.S.C. 154(b) by 130 days.

This patent is subject to a terminal disclaimer.

(21) Appl. No.: 12/693,753

(22) Filed: Jan. 26, 2010

(65) Prior Publication Data
US 2010/0189808 A1 Jul. 29, 2010

Related U.S. Application Data

(60) Provisional application No. 61/147,658, filed on Jan. 27, 2009, provisional application No. 61/150,488, filed on Feb. 6, 2009.

(51) Int. Cl.
| | | |
|---|---|---|
| *A61K 31/737* | (2006.01) | |
| *A61K 33/04* | (2006.01) | |
| *A61K 33/20* | (2006.01) | |
| *A61K 33/18* | (2006.01) | |
| *A61K 33/40* | (2006.01) | |
| *A61K 33/38* | (2006.01) | |
| *A61K 33/24* | (2006.01) | |
| *A61P 31/04* | (2006.01) | |
| *A61P 11/00* | (2006.01) | |
| *A61P 11/10* | (2006.01) | |
| *A61M 1/00* | (2006.01) | |
| *A61M 35/00* | (2006.01) | |

(52) U.S. Cl.
USPC .......... 424/616; 424/713; 424/665; 424/661; 424/667; 424/670; 424/618; 424/653; 514/59; 604/523; 604/1; 15/167.1

(58) Field of Classification Search
None
See application file for complete search history.

(56) References Cited

U.S. PATENT DOCUMENTS

| | | | | |
|---|---|---|---|---|
| 2,715,091 | A | * 8/1955 | Ricketts et al. | ................. 514/59 |
| 4,867,897 | A | * 9/1989 | Kolstad | ......................... 424/662 |
| 5,688,516 | A | * 11/1997 | Raad et al. | ..................... 424/409 |
| 5,750,340 | A | * 5/1998 | Kim et al. | ..................... 435/6.13 |
| 6,015,836 | A | 1/2000 | Martin | |

(Continued)

FOREIGN PATENT DOCUMENTS

WO    WO00/10385    * 3/2000    ............ A01M 59/00

OTHER PUBLICATIONS

Madison Sheely, Glycerol Viscosity Tables, 24 Indust. Eng. News 1060 (1932).*

(Continued)

*Primary Examiner* — Ernst Arnold
*Assistant Examiner* — Jianfeng Song
(74) *Attorney, Agent, or Firm* — Baker & Hostetler LLP

(57) ABSTRACT

A composition for dissolving or reducing the viscosity of sputum on a surface of a device includes an effective amount of glycerol and an effective amount of dextran sulfate in a saline solution. The effective amount of glycerol is between about 30-50% and the effective amount of dextran sulfate is between about 10-30%. The composition may further include an antimicrobial agent.

13 Claims, 8 Drawing Sheets

Saline

40% Glycerol

40% Glycerol + 5% DexS

40% Glycerol + 20% DexS

(56) References Cited

U.S. PATENT DOCUMENTS

| | | | |
|---|---|---|---|
| 7,255,891 B1 | 8/2007 | Pacetti | |
| 7,607,436 B2 | 10/2009 | Smaldone et al. | |
| 2003/0225394 A1* | 12/2003 | Ahnblad et al. | 604/514 |
| 2004/0063110 A1* | 4/2004 | Stender et al. | 435/6 |
| 2004/0224922 A1* | 11/2004 | King | 514/59 |
| 2004/0241734 A1* | 12/2004 | Davis | 435/6 |
| 2004/0265934 A1* | 12/2004 | Stender et al. | 435/7.32 |
| 2008/0199623 A1 | 8/2008 | Terry | |
| 2010/0191219 A1* | 7/2010 | Gupta et al. | 604/508 |

OTHER PUBLICATIONS

Dickinson, et al., "Oral Care During Mechanical Ventilation: Critical for VAP Prevention." Society for Critical Care Medicine, Feb. 2008, pp. 8-9.

International SearchReport for PCT/US10/22041, dated Mar. 1, 2010.

* cited by examiner

SPUTUM DISSOLVING SUCTIONING SOLUTION FOR ENDOTRACHEAL AND TRACHEOSTOMY TUBES

CROSS-REFERENCE TO RELATED APPLICATIONS

This application claims priority to provisional U.S. patent application filed Jan. 27, 2009, having a Ser. No. 61/147,658 and to provisional U.S. patent application filed Feb. 6, 2009, having a Ser. No. 61/150,488, the disclosures of which are hereby incorporated by reference in their entirety.

FIELD OF THE INVENTION

The present invention relates generally to medical and respiratory devices. More particularly, the present invention relates to endotracheal or tracheostomy tubes and a system, device, and method for reduction of mucus or sputum on a surface thereof.

BACKGROUND OF THE INVENTION

This invention relates to a composition that is used in connection with medical devices that are in contact with sputum, such as endotracheal or tracheostomy tubes. Patients who require mechanical ventilations are often intubated with endotracheal or tracheostomy tubes. The formation of mucus in the respiratory tract is a normal part of host defense. Sputum is an accumulation of mucus that cannot be easily removed from the respiratory tract by normal mucociliary clearance. Sputum is usually cleared by a deep cough. Thus, in a mechanically ventilated patient, the endotracheal intubation greatly compromises the normal mucociliary transport system leading to build-up of large volumes of sputum in the lungs. Mucus build-up in conjunction with implanted airway devices also leads to blockage in an evacuation tube.

Furthermore, secretions from the oral cavity can get accumulated on the cuff of the endotracheal tube (ETT). Continuous exposure of the lower respiratory tract to large numbers of potential pathogens through the endotracheal tube and the micro aspiration (leakage) around the cuff into the lower respiratory tract can lead to air way infection or ventilator associated pneumonia (VAP).

VAP is considered one of the most serious and costly hospital-acquired infections. Approximately 8-28% of patients on ventilators develop VAP, which adds at least $20,000-40,000 to the cost of care. Thus, the removal of the sputum build-ups on or around an inserted ETT can prevent VAP and therefore lower the cost of health care. Moreover, the removal of sputum allows the evacuation tube to perform properly.

Known attempts to solve this problem have resulted in the use of saline solution as a suctioning solution by the care provider to loosen or dissolve the mucus build-up. In such a method, suction catheters are inserted into the trachea, and either continuous or intermittent vacuum or manual suctioning is applied to remove the sputum through the lumen of the ETT. Suctioning is also performed to remove secretions that get accumulated on the cuff of the ETT. Often, the accumulated sputum is too thick and viscous to be easily moved. Another complication that arises in ETTs with subglottic suctioning portions, lumens, and connector (i.e., EVAC tubes), particularly in the practice of continuous suctioning, is that it can lead to buildup of layers of dried secretions on the ETT cuff that can completely clog the suction portion of the subglottic suctioning ETT. Therefore, the use of saline is inefficient and cumbersome.

Therefore, there exists a problem with intubation where sputum and mucus buildup on the intubation tube cause pneumonia and the removal of which using saline solution is ineffective and burdensome. It is desirable therefore to provide a sputum dissolving suctioning solution to be used on the intubation tube that decreases the viscosity of the sputum, thus allowing effective removal of the sputum and mucus buildup from the tube.

Accordingly, it is desirable to provide a composition for dissolving sputum on a surface of a medical device and a method of using the same.

SUMMARY OF THE INVENTION

The foregoing needs are met, to a great extent, by the present invention, wherein in one aspect a composition for dissolving or reducing the viscosity of sputum on surface of a device is provided. In some embodiments the present invention provides an effective amount of glycerol and an effective amount of dextran sulfate in a saline solution. The effective amount of glycerol is between about 30-50% and the effective amount of dextran sulfate is between about 10-30%. The saline solution is at least about 0.85%. The composition further provides for possible inclusion of one or more antimicrobial agents.

An embodiment of the present invention pertains to a method for removing mucus from a surface of a device inside a trachea. The method includes applying a composition to the surface of the device to dissolve the mucus. The composition includes an effective amount of glycerol and an effective amount of dextran sulfate in a saline solution. The method further includes allowing the mucus to dissolve and removing the mucus from the trachea.

Another embodiment of the present invention relates to a method for removing built-up sputum or mucus from a surface of a tracheal cuff tube or in a lumen of a tube inside a trachea of a patient. The method includes applying a composition to the surface of the tracheal cuff tube or in the lumen of the tube to dissolve the built-up sputum or mucus. The composition includes an effective amount of glycerol and an effective amount of dextran sulfate in a saline solution. The method further includes allowing the built-up sputum or mucus to dissolve and suctioning the built-up sputum or mucus from the surface.

Yet another embodiment of the present invention pertains to a kit. The kit includes a suctioning catheter and a sputum dissolving solution having an effective amount of glycerol and an effective amount of dextran sulfate in a saline solution.

Yet another embodiment of the present invention pertains to a VAP prevention kit. The VAP prevention kit includes a sputum dissolving solution having an effective amount of glycerol and an effective amount of dextran sulfate in a saline solution and oral prophylaxis items. The oral prophylaxis items includes at least a tooth brush, a swab, and disinfecting mouth rinse.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

An embodiment of the invention includes a composition for dissolving or reducing the viscosity of sputum on a surface of a medical device. The composition includes an effective amount of glycerol and an effective amount of dextran sulfate in a saline solution. As shown and described herein, the effective amount of glycerol is between about 30-50%. The effective amount of dextran sulfate is between about 10-30%. The effective amount of saline solution is at least about 0.85%. The composition as disclosed can have an effective amount of glycerol at about 40% and an effective amount of dextran sulfate at about 20% in saline solution. In this composition, glycerol is used as an anti-drying agent to moisten the mucus or rewets it if dried deposits have formed and dextran sulfate is used as a dissolving agent to reduce the viscosity of the sputum on the endotracheal tube (ETT). This unique and novel combination of glycerol, dextran sulfate, and saline works in synergy and effectively loosens the mucus build-up on the surfaces of the endotracheal or tracheostomy tubes and allows the caretaker to easily remove the mucus using a suctioning device. Furthermore, the use of this composition minimizes the "microaspiration" linked ventilator associated pneumonia (VAP) episodes and improve the airway management.

In addition to dissolving or reducing the viscosity of sputum, the composition can further include compounds of agents that prevent infection (e.g., antimicrobial agents and antibiotics), chemotherapeutic agents, antiseptics, antimicrobial dyes, or other biocides. The compounds of agents used with the composition can include, inter alia, a member selected from the group consisting of a taurinamide derivative, a phenol, quaternary ammonium surfactant, chlorine-containing, quinoline, quinaldinium, lactone, dye, thiosemicarbazone, quinone, sulfa, carbamates, urea, salicylamide, carbanilide, amide, guanide, amidine, chelate, imidazoline biocides, acetic acid, benzoic acid, sorbic acid, propionic acid, boric acid, dehydroacetic acid, sulfurous acid, vanillic acid, esters of p-hydroxybenzoic acid, ethanol, isopropanol, propylene glycol, benzyl alcohol, chlorobutanol, phenylethyl alcohol, 2-bromo-2-nitropropan-1,3-diol, formaldehyde, glutaraldehyde, calcium hypochlorite, potassium hypochlorite, sodium hypochlorite, iodine (in various solvents), povidone-iodine, hexamethylenetetramine, noxythiolin, 1-(3-choroallyl)-3,5,7-triazo 1-azoniaadamantane chloride, taurolidine, taurultam, ethylenediaminetetraacetic acid (EDTA), N(5-nitro-2-furfurylidene)-1-amino-hydantoin, 5-nitro-2-furaldehyde semicarbazone, 3,4,4'-trichlorocarbanilide, 3,4',5-tribromosalicylanilide, salicylanilide, 3-trifluoromethyl-4,4'-dichlorocarbanilide, 8-hydroxyquinoline, 1-cyclopropyl-6-fluoro-1,4-dihydro-4-oxo-7-(1-piperazinyl)-3-quinolinecarboxylic acid, 1,4-dihydro-1-ethyl-6-fluoro-4-oxo-7-(1-piperazinyl)-3-quinolinecarboxylic acid, hydrogen peroxide, peracetic acid, phenol, sodium oxychlorosene, parachlorometaxylenol, 2,4,4'-trichloro-2'-hydroxydiphenol, thymol, chlorhexidine, benzalkonium chloride, cetylpyridinium chloride, silver, nanosilver, silver sulfadiazine, silver nitrate, 5 fluorouracil, phenolic antiseptics, gentian violet, methylene blue, brilliant green, and bismuth compounds.

Methods of Use

In operation, a care provider applies the present inventive composition having an effective amount of glycerol and an effective amount of dextran sulfate in saline solution to the surface of the endotracheal tube or the tracheostomy tube. The composition is allowed time to dissolve and moisten any dried-up sputum for about 5 to 15 minutes. For thick sputum that is not completely dried, the application of the inventive composition to the sputum thins the sputum on contact or instantly. Once the sputum is dissolved or thinned, the sputum is removed using a suctioning device.

The inventive composition can also dissolve the dried sputum or mucus from the surface of a tracheal cuff tube or in the lumen of the tube. For example, the composition is applied to the surface of the tracheal cuff tube or placed in the lumen of the tube and allowed to dissolve and soften the dried sputum. In response to dissolving or softening the sputum, the sputum may be removed using a suctioning device.

Kit

Another embodiment of the invention includes kits containing the composition and an apparatus used by the care provider or the patient. In a particular example, the kit includes a suctioning catheter and the sputum dissolving solution. In a preferred example, the suctioning catheter can be disposed of after use to reduce or prevent contamination and reduce risk of infection.

In another embodiment according to the present invention, the kit includes the sputum dissolving solution and oral prophylaxis items, such as a tooth brush, a swab, and disinfecting mouth rinse. The use of these items in conjunction with the sputum dissolving solution improves the oral hygiene of the patient.

Methods And Results

Example 1

Evaluation of Agents On Sputum Hydration/Dissolution

Test solutions containing different concentrations of glycerol and dextran sulfate (w/v) were prepared in 0.85% normal saline. All steps were performed at 37° C. unless specified otherwise. Each well of a 48 well microtitre plate was pre-wetted with a test solution for 2 hours. Human sputum (20 μl) was then allowed to dry for 2 hours on the pre-wetted surface, followed by incubation with 100 μl of the test solution for 15 minutes to dissolve the dried sputum, and subsequent removal of the solution. The complete cycle of sputum drying, incubation with the test solution and removal, was repeated three times. In the third and final cycle, the dried sputum was incubated with the test solution overnight instead of 15 minutes. Visual observations were recorded at each cycle and pictures were taken under a microscope.

Figure 1:
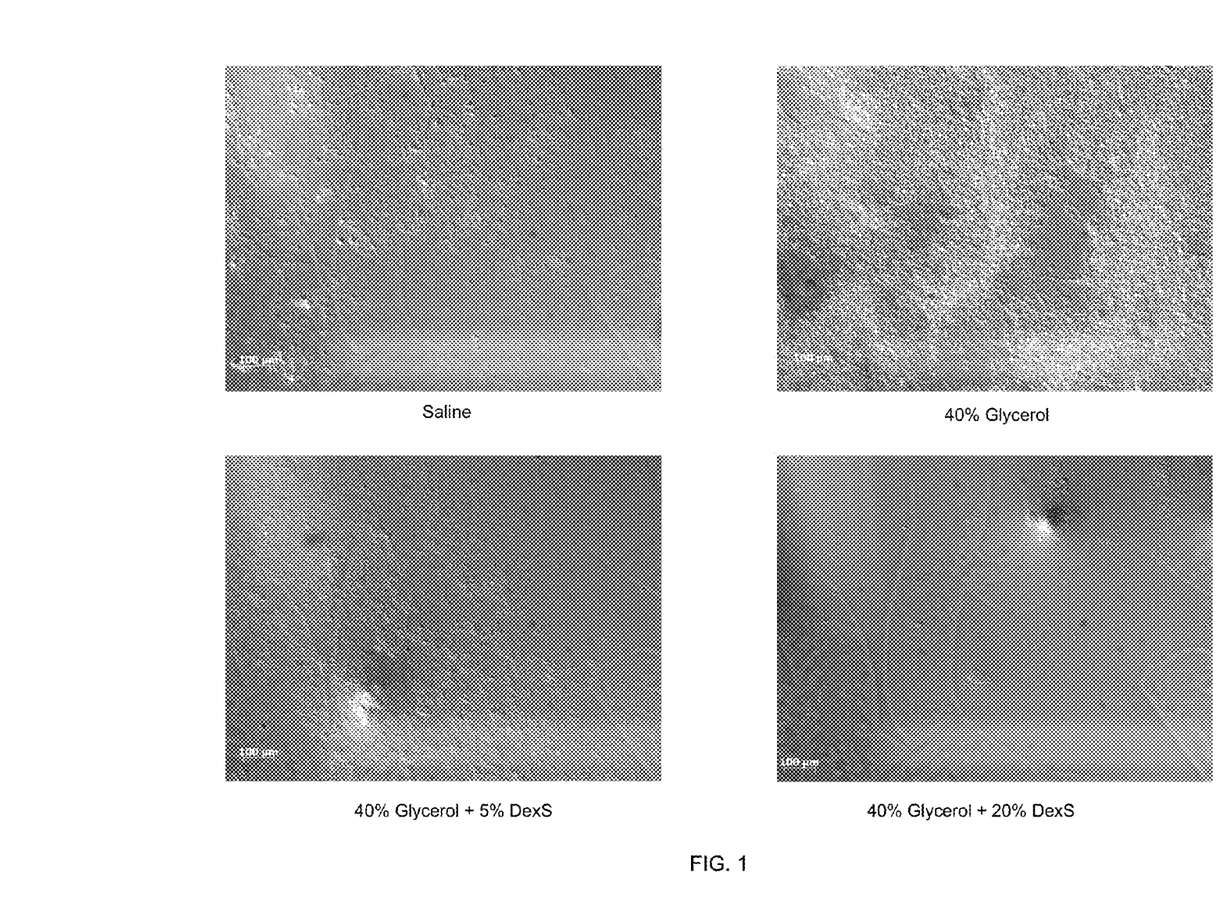
FIG. 1 is a series of photomicrographs of microtitre plates taken after the completion of the third cycle with different treatments according to the process described in Example 1.

FIG. 1 is a series of photomicrographs of microtitre plates taken after the completion of the third cycle with different treatments according to the process described in Example 1. The results as shown in FIG. 1 and the following Tables 1-3 indicate that the combination of 40% glycerol and 20% dextran sulfate is the most effective solution in dissolving dried sputum compared to the solutions containing either saline, glycerol or dextran sulfate alone.

TABLE 1

| Glycerol alone | | | |
|---|---|---|---|
| Glycerol Concentration | Cycle 1 | Cycle 2 | Cycle 3 |
| 0.1% | + | ++ | ++ |
| 10.0% | − | ++ | ++ |
| 30.0% | − | + | ++ |
| 40.0% | − | − | ++ |
| .85% saline only | − | ++ | ++ |

− No residue left
+ Very slight residue left
++ Residue left

TABLE 2

| Dextran sulfate (8 kDa) alone | | | |
|---|---|---|---|
| Dextran sulfate concentration | Cycle 1 | Cycle 2 | Cycle 3 |
| 1.0% | − | ++ | ++ |
| 5.0% | − | ++ | + |
| 10.0% | − | ++ | ++ |
| 20.0% | − | + | ++ |
| .85% saline only | − | ++ | ++ |

− No residue left
+ Very slight residue left
++ Residue left

TABLE 3

| 40% glycerol in combination with dextran sulfate | | | |
|---|---|---|---|
| Dextran sulfate concentration | Cycle 1 | Cycle 2 | Cycle 3 |
| 0.1% | + | + | + |
| 1.0% | − | − | + |
| 5.0% | − | − | + |
| 20.0% | + | − | − |
| .85% saline only | − | ++ | ++ |

− No residue left
+ Very slight residue left
++ Residue left

Table 1 shows that by using concentrations of 0.1%, 10%, 30%, and 40% glycerol alone, after three cycles of drying, incubating with and removal of solvent, the microtitre plates contain sputum residue. Table 2 shows that by using concentrations of 1%, 5%, 10%, and 20% dextran sulfate alone, after three cycles of drying, incubating with and removal of solvent, the microtitre plates contain sputum residue. In contrast to Tables 1 and 2, Table 3 shows that by using 40% glycerol in combination with 0.1%, 1%, 5%, or 20% dextran sulfate, achieves and unexpected and synergistic reduction or elimination of sputum residue in wells of the microtitre plate. The combination of 40% glycerol with 20% dextran sulfate is the most effective at dissolving dried sputum.

Example 2

Effective Concentration of Glycerol

To closely mimic clinical practice, a few modifications were made in the method used in Example 1. Sputum was dried for 4 hours instead of 2 hours in each cycle, and in the third cycle dried sputum was incubated with the test solution for only 15 minutes instead of an overnight incubation. The rest of the method is the same as in Example 1.

Figure 2:
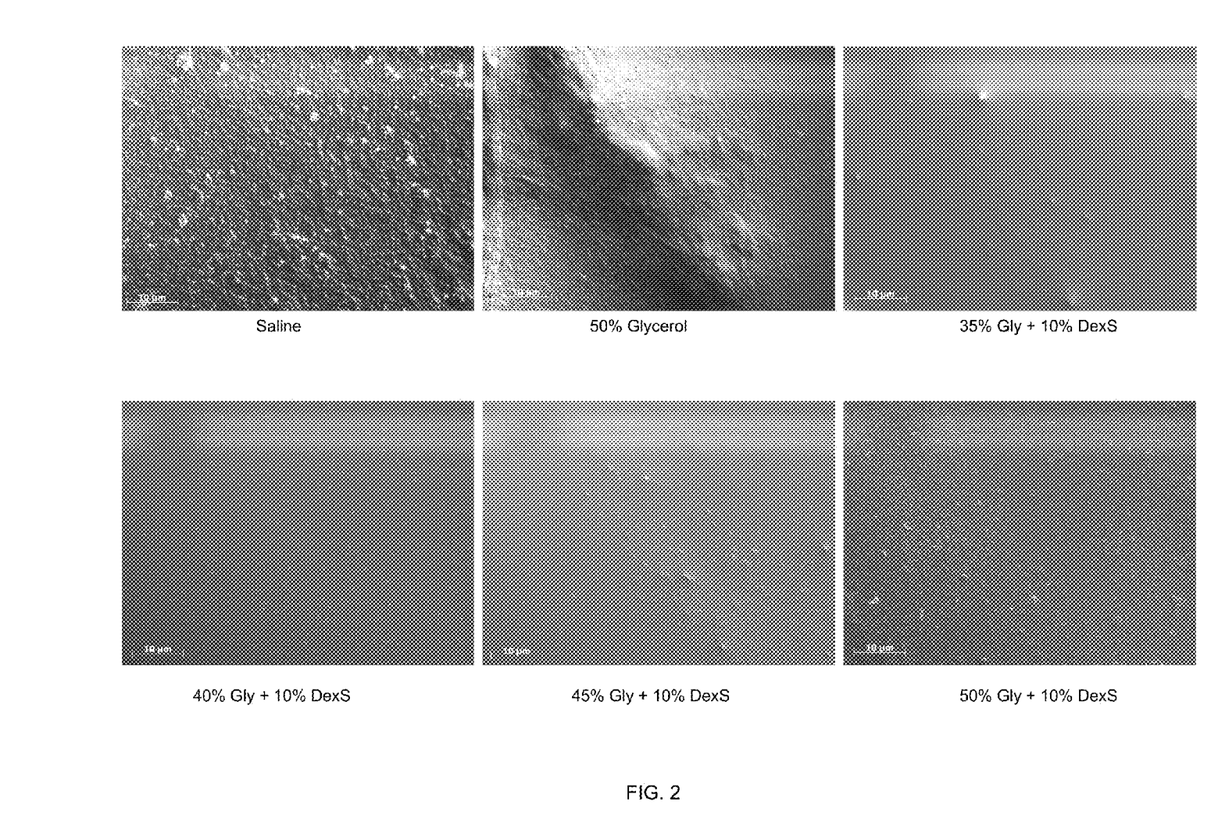
FIG. 2 is a series of photomicrographs of microtitre plates taken after the completion of the third cycle with different treatments according to the process described in Example 2.

FIG. 2 is a series of photomicrographs of microtitre plates taken after the completion of the third cycle with different treatments according to the process described in Example 2. All the test solutions contained 0.85% of NaCl.

By using 0.85% saline alone, the plate contains residue of dried sputum. Similarly, the plate using 50% glycerol also contains residue of dried sputum. In comparison, the combination of glycerol and dextran sulfate (35% glycerol+10% dextran sulfate, 40% glycerol+10% dextran sulfate, 45% glycerol+10% dextran sulfate, and 50% glycerol+10% dextran sulfate) far outperforms saline alone. The dissolution of sputum dried over a long period of time can be achieved by the glycerol and dextran sulfate combination in a relatively short period of time. The most effective range for glycerol is 30-50% and for dextran sulfate is 10-20%.

Example 3

Effective Concentration of NaCl

To find an effective concentration range of sodium chloride, solutions containing 40% glycerol, 10% dextran sulfate and different amounts of sodium chloride were prepared, and subsequently same method was followed as in Example 2.

Figure 3:
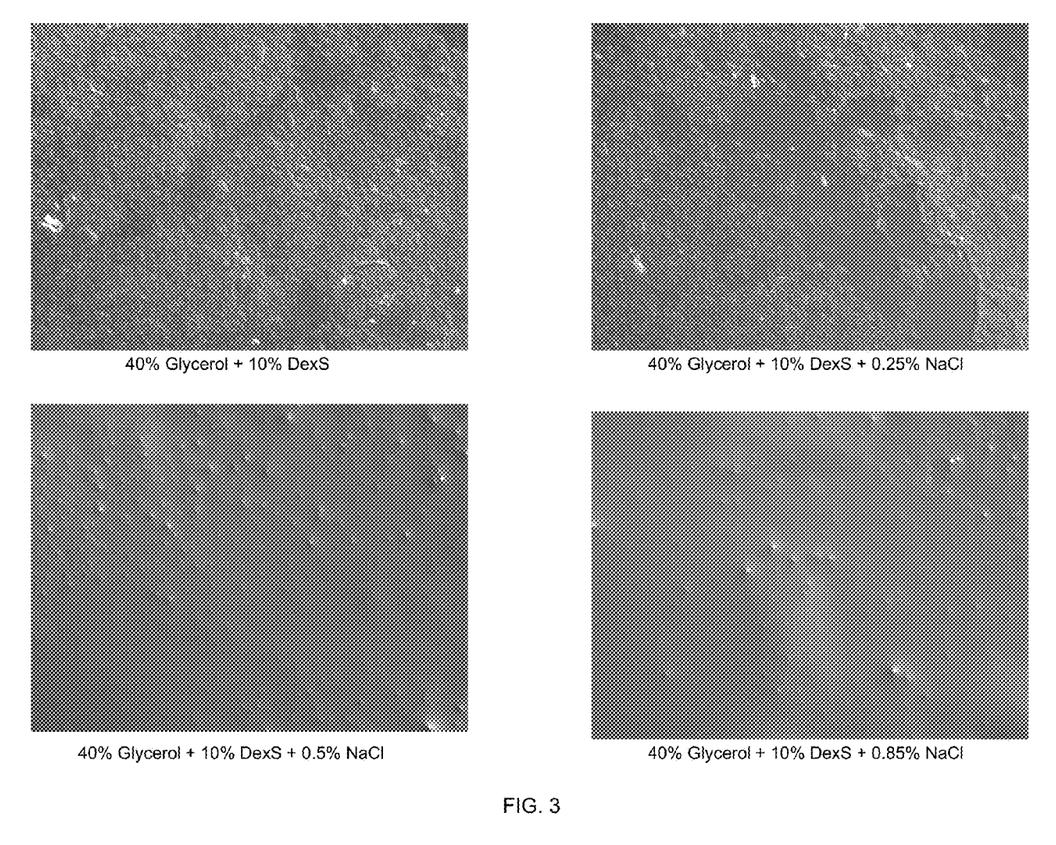
FIG. 3 is a series of photomicrographs of microtitre plates taken after 5 minutes of exposure to mixtures of 40% glycerol and 10% dextran sulfate in different concentrations of saline solutions.

FIG. 3 is a series of photomicrographs of microtitre plates taken after 5 minutes of exposure to mixtures of 40% glycerol and 10% dextran sulfate in different concentrations of saline solutions at cycle 2 according to the process described in Example 2. As shown in FIG. 3, the plate with 40% glycerol and 10% dextran sulfate without any saline has the most sputum residue. In comparison, the plate with an addition of 0.85% saline solution shows the most effective result. The minimum amount required to effectively dissolve the residues of dried sputum is a sodium chloride concentration greater than 0.5% (w/w).

Example 4

Evaluation of the Safety of the Sputum Dissolving Suctioning Solution in a Pig Model A Sheridan/HVT 9.6 mm endotracheal tube (ETT) was placed in a 50 kg female Yorkshire pig. Baseline oxygen saturation via pulse oximetry was recorded. Various test solutions were administered through the endotracheal tube via a 10 Fr suction catheter. After a time period of 5 minutes the solution was suctioned from the ETT using the 10 Fr catheter.

The oxygen saturation was determined immediately before and after suctioning, and then at 1 minute intervals until the baseline was reached. Once the baseline was achieved, the next solution was tested either directly, or after lavaging the lungs with saline between suctioning episodes.

TABLE 4

Comparison of glycerol concentrations in a pig model

| Solution Id | Starting $O_2$ Sat (%) | $O_2$ Sat following instillation (%) | Time to return to baseline |
|---|---|---|---|
| Saline | 100 | 100 | None |
| 40% glycerol + 20% dextran sulfate | 100 | 100 | None |
| 30% glycerol + 20% dextran sulfate | 100 | 98 | 5 sec |

The solutions containing glycerol and dextran sulfate did not adversely affect the oxygen saturation levels and were safe as shown in Table 4. Thus, a combination of an effective amount of glycerol and an effective amount of dextran sulfate in saline solution can successfully dissolve dried sputum. Specifically, the combination of 30-40% glycerol+10-20% dextran sulfate in 0.85% saline can be used as a sputum hydrating/dissolving suctioning solution. This solution can minimize the risk of ventilator associated pneumonia (VAP) by preventing drying of secretions on the ETT cuff and by facilitating efficient removal by thinning thick respiratory secretions.

Example 5

Effect of Sputum Dissolving Suctioning Solution Containing Iodine On Planktonic Microorganism Lugol's solution, routinely used for disinfection contains iodine and potassium iodide at 1:2 ratio in water. Solutions containing varying concentration of iodine ($I_2$) and potassium iodide (KI) were tested against *Klebsiella pneumonia*, a gram negative VAP pathogen to determine an effective ratio of iodine and potassium iodide in combination with the sputum dissolving solution.

Briefly, wells of a 48-well plate were filled with 1 mL each of the of the antimicrobial sputum dissolving solution containing 50% glycerol+0.85% NaCl+10% Dextran sulfate+ 0.001-2 mg/mL $I_2$+0.001-2 mg/mL KI or the control solution which is 0.85% saline, followed by addition of $10^6$ colony forming units per milliliter (CFU/mL) of *K. pneumoniae*. Subsequently, after 2 minutes of incubation an aliquot of 10 μL from each well was removed and serially diluted in PBS. 10 μL of each dilution was then plated onto the surface of Dey Engley neutralizing agar (D/E). Plates were inverted and incubated at 37° C. for 24 hours. Subsequently, the number of colonies per plate was recorded and CFU/mL was determined. Each test was run in triplicate.

Figure 4:
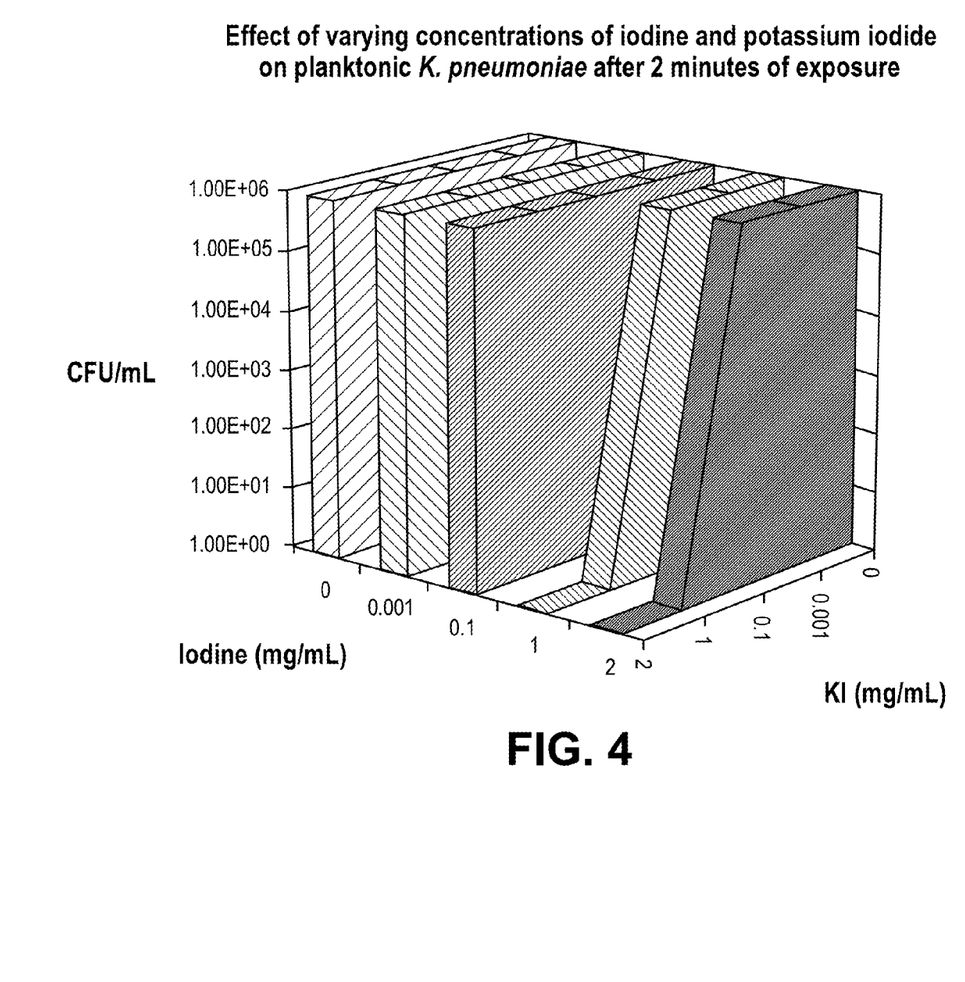
FIG. 4 is a chart showing the effect of varying concentrations of iodine and potassium iodide on planktonic $K.$ $pneumoniae$ after 2 minutes of exposure.

Sputum dissolving solutions containing Iodine and KI either at 1:1 or 1:2 ratios were equally effective in killing *K. pneumoniae* within 2 minutes of exposure as shown in FIG. 4. Iodine and KI at a ratio of 1:2 was selected for all further testing.

Solutions containing 50% glycerol+0.85% NaCl+10% Dextran sulfate+0.1-1 mg/mL $I_2$+0.2-2 mg/mL KI were further tested against other VAP pathogens, such as *Staphylococcus aureus* (SA), *Acinetobacter baumannii* (AB), *Escherichia Coli* (EC), Vancomycin-Resistant *Enterococcus* (VRE), *Enterococcus faecium* (EF), *Pseudomonas aeruginosa* (PA), and *Klebsiella pneumonia* (KP).

Figure 5:
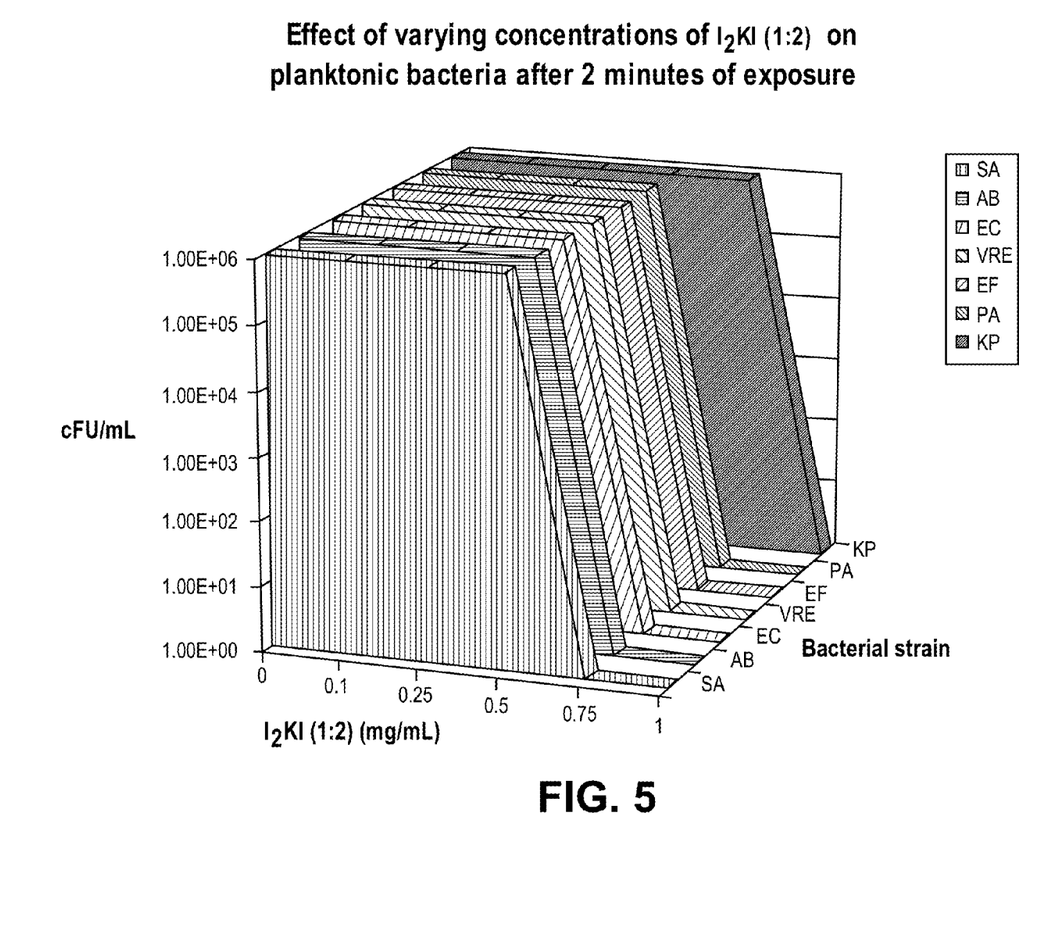
FIG. 5 is a chart showing the effect of varying concentrations of iodine on several planktonic bacteria species after 2 minutes of exposure.

Except *K. pneumoniae* all other six bacterial strains were killed within 2 minutes of exposure to the solutions containing 0.75 mg/mL Iodine/KI (1:2). For complete killing of *K. pneumoniae*, slightly higher concentration of Iodine which was at 1 mg/mL was required as shown in FIG. 5.

Example 6

Effect of Sputum Dissolving Suctioning Solution Containing Iodine On Pre-Formed Biofilm Pre-formed mature biofilm of the above seven organisms were exposed for 15 minutes to 50% glycerol+0.85% NaCl+ 10% Dextran sulfate+0.1-1 mg/mL $I_2$+0.2-2 mg/mL KI or the control solution which is 0.85% saline. Briefly, $10^6$ CFU/mL of a test organism was added into each well of a polystyrene 96-peg plate. Biofilm was allowed to grow on the pegs of the lid for 24 hours. Subsequently the lid with the pegs was removed from the plate and immersed for 15 minutes in another 96 well plate containing with various $I_2$/KI solutions. The PEG lid was then removed again and placed on another 96 well plate containing 1 mL of D/E broth in each well. The plates were sonicated for 20 minutes and then 10 μl from each well was removed and plated onto the surface of D/E agar. Plates were inverted and incubated at 37° C. for 24 hours. Subsequently number of colonies per plate was recorded and CFU/mL was determined. Each test was run in triplicate.

Figure 6:
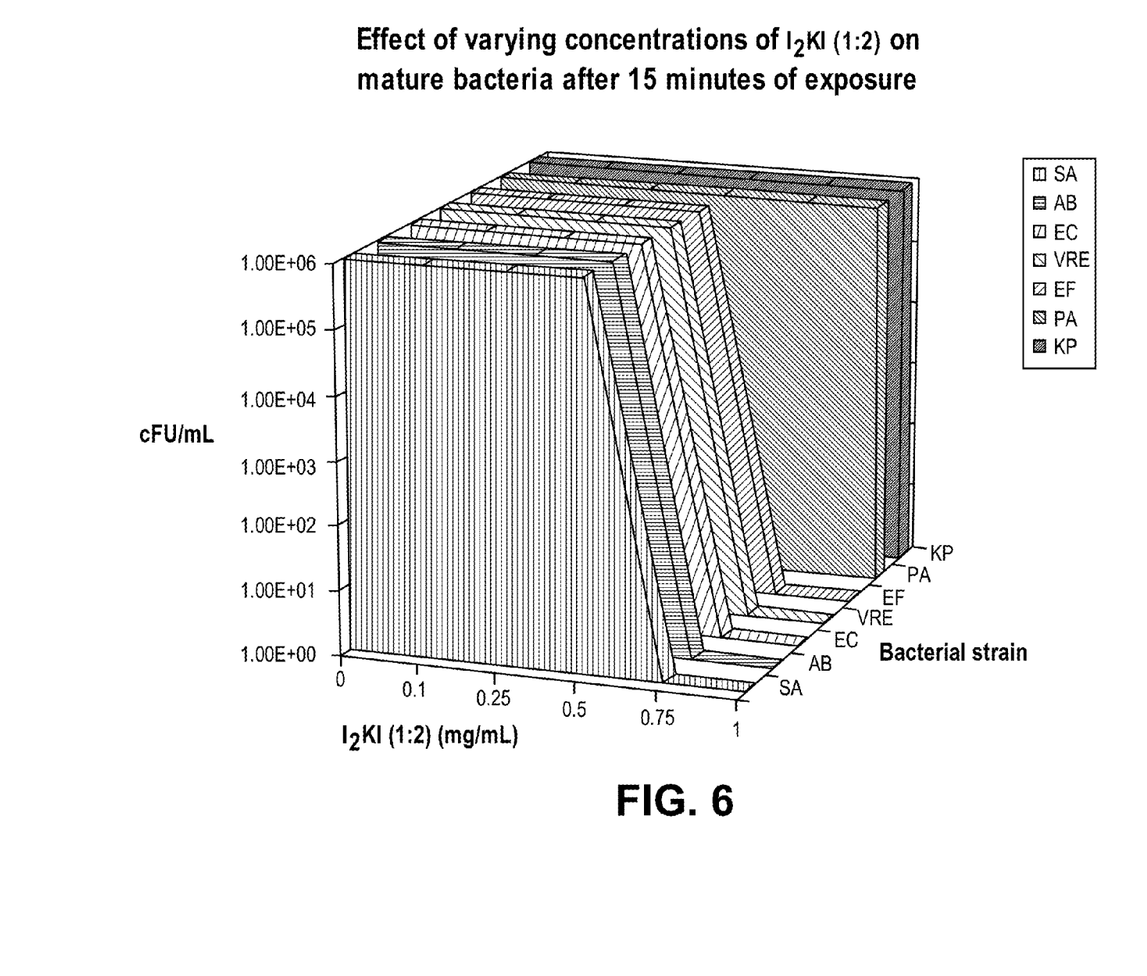
FIG. 6 is a chart showing the effect of varying concentrations of iodine on mature biofilms of several bacteria species after 15 minutes of exposure.
Figure 7:
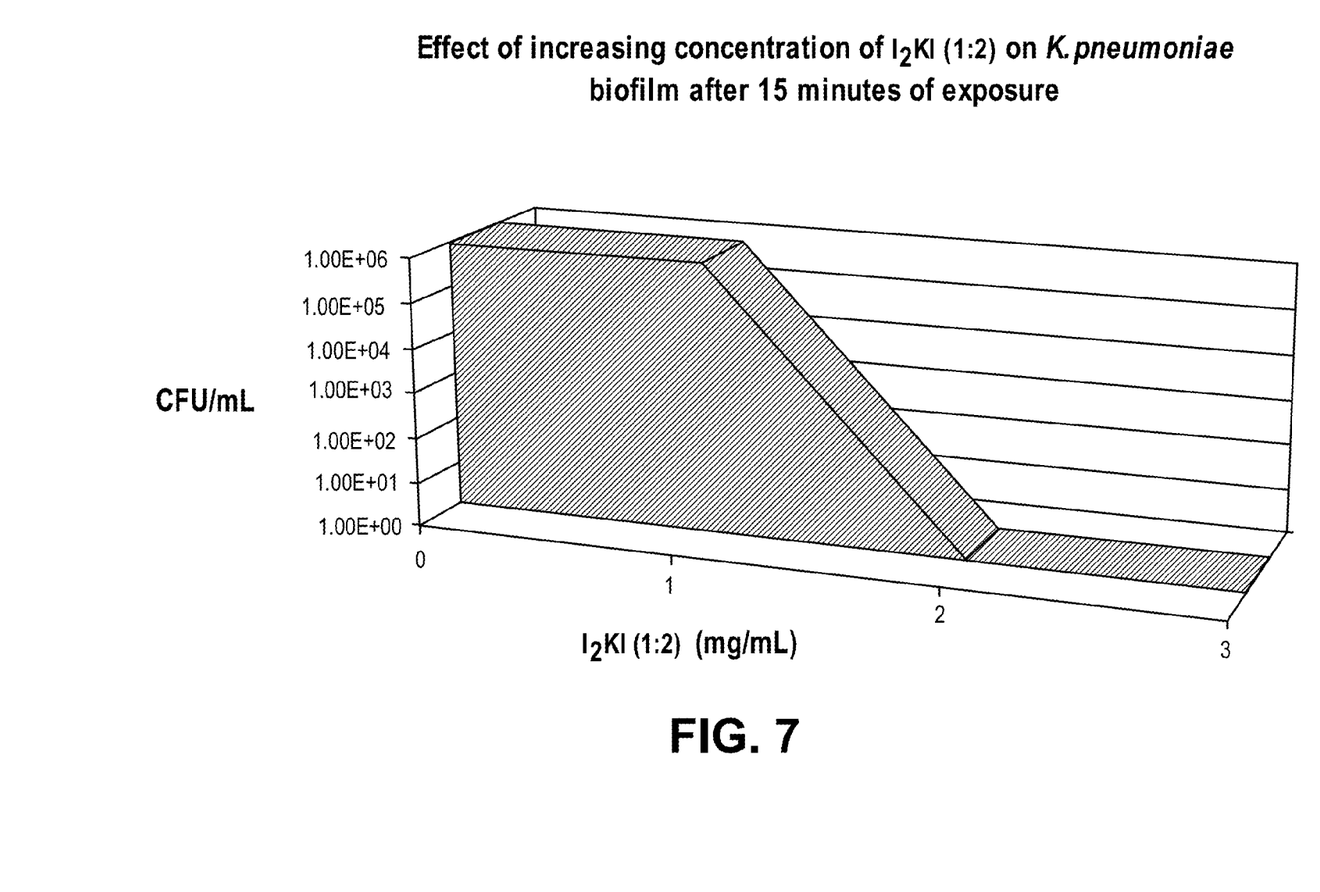
FIG. 7 is a chart showing the effect of increasing concentrations of iodine on mature biofilms of $K.$ $pneumoniae$ after 15 minutes of exposure.

All bacterial biofilm except *K. pneumoniae* and *P. aeruginosa* could be eradicated within 15 minutes of exposure to the solutions containing 0.75 mg/mL Iodine and KI (1:2) as shown in FIG. 6. *K. pneumoniae* biofilm was eradicated when concentration of iodine was increased to 2 mg/mL as shown in FIG. 7.

Example 7

Effect of Sputum Dissolving Suctioning Solution Containing Iodine On the Endotracheal Tube (ETT) Cuff Biofilm To evaluate the performance of the sputum dissolving containing iodine, under sterile conditions, an ETT was inserted into a 100 mL cylinder and cuff was inflated using 20 cc of air. Thereafter 5 mls of tryptic soy broth inoculated with $10^6$ CFU of *K. pneumoniae* was placed on the inflated cuff. The whole set-up was then placed in a sterile pouch and incubated at 37° C. for 24 hrs to allow growth of biofilm on the ETT cuff. After 24 hrs, the media was removed and cuff was partially deflated. The partially deflated cuff was then transferred in 50 mL conical tubes containing either 30 mL saline, 5 mg/mL $I_2$/KI (1:2), or 10 mg/mL $I_2$/KI (1:2). After 15 minutes of incubation, cuff was transferred in another 50 mL conical tube containing 35 mL of D/E Broth, sonicated for 20 minutes and then 100 µl was plated on D/E agar. Plates were inverted and incubated at 37° C. for 24 hours. Subsequently number of colonies per plate was recorded and CFU/mL was determined. Each test was run in triplicate.

Figure 8:
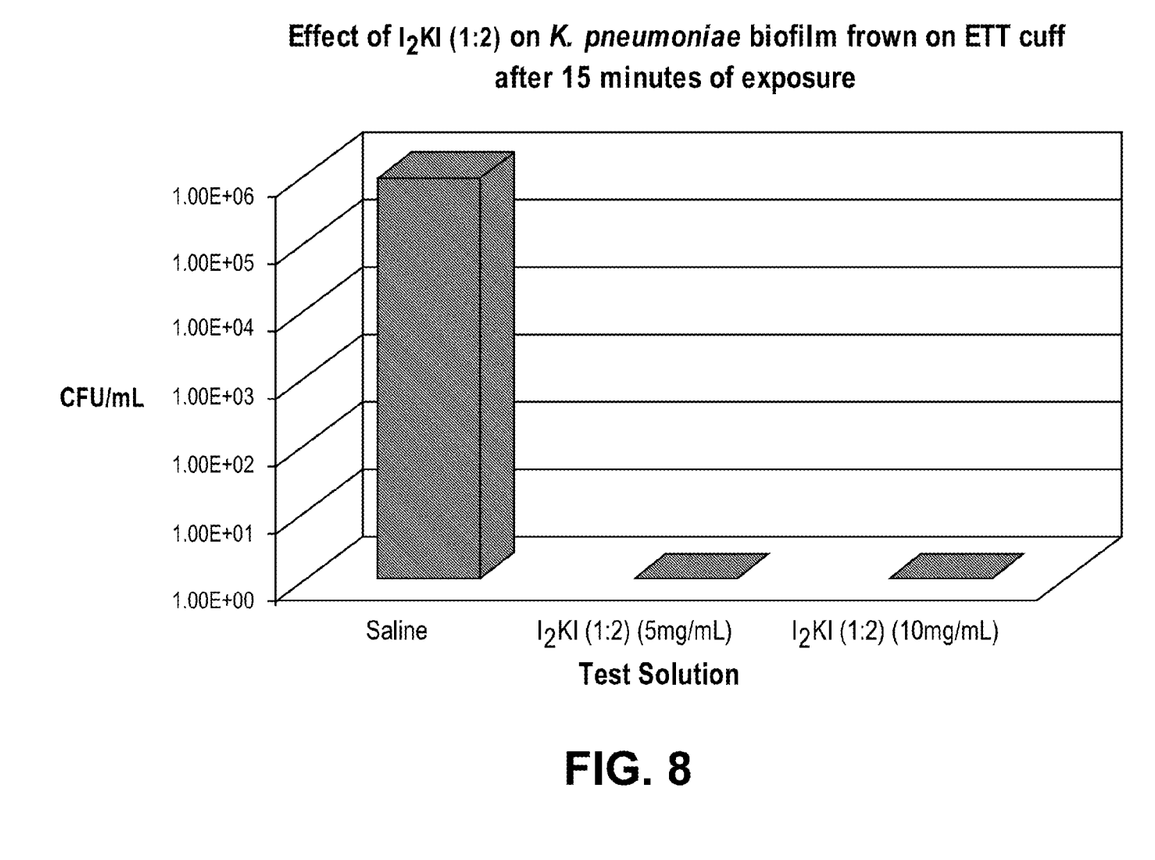
FIG. 8 is a chart showing the effect of increasing concentrations of iodine on mature biofilms of $K.$ $pneumoniae$ grown on endotracheal tube cuff after 15 minutes of exposure.

Mature biofilm of *K. pneumoniae* growing on the ETT cuff were completely eradicated within 15 minutes of exposure to the sputum dissolving solution containing at least 5 mg/mL of Iodine/KI (1:2) as shown in FIG. 8.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A composition for dissolving or reducing the viscosity of sputum on a surface of a device, the composition comprising:
    an effective amount of glycerol and an effective amount of dextran sulfate in a saline solution to dissolve or reduce the viscosity of sputum and improve the function of the device, wherein the effective amount of glycerol is 50%, the effective amount of dextran sulfate is 20%, and the amount of salt in the saline solution is at least 0.85%; and
    a chlorhexidine.

2. The composition according to claim 1, further comprising one or more antimicrobial agents.

3. The composition according to claim 2, wherein the antimicrobial agent is selected from a group consisting of a taurinamide derivative, a phenol, quaternary ammonium surfactant, chlorine-containing, quinoline, quinaldinium, lactone, dye, thiosemicarbazone, quinone, sulfa, carbamates, urea, salicylamide, carbanilide, amide, guanide, amidine, chelate, imidazoline biocides, acetic acid, benzoic acid, sorbic acid, propionic acid, boric acid, dehydroacetic acid, sulfurous acid, vanillic acid, esters of p-hydroxybenzoic acid, ethanol, isopropanol, propylene glycol, benzyl alcohol, chlorobutanol, phenylethyl alcohol, 2-bromo-2-nitropropan-1,3-diol, formaldehyde, glutaraldehyde, calcium hypochlorite, potassium hypochlorite, sodium hypochlorite, iodine (in various solvents), povidone-iodine, hexamethylenetetramine, noxythiolin, 1-(3-choroallyl)-3,5,7-triazo 1-azoniaadamantane chloride, taurolidine, taurultam, EDTA, N(5-nitro-2-furfurylidene)-1-amino-hydantoin, 5-nitro-2-furaldehyde semicarbazone, 3,4,4'-trichlorocarbanilide, 3,4',5-tribromosalicylanilide, salicylanilide, 3-trifluoromethyl-4,4'-dichlorocarbanilide, 8-hydroxyquinoline, 1-cyclopropyl-6-fluoro-1,4-dihydro-4-oxo-7-(1-piperazinyl)-3-quinolinecarboxylic acid, 1,4-dihydro-1-ethyl-6-fluoro-4-oxo-7-(1-piperazinyl)-3-quinolinecarboxylic acid, hydrogen peroxide, peracetic acid, phenol, sodium oxychlorosene, parachlorometaxylenol, 2,4,4'-trichloro-2'-hydroxydiphenol, thymol, benzalkonium chloride, cetylpyridinium chloride, silver, nanosilver, silver sulfadiazine, silver nitrate, 5 fluorouracil, phenolic antiseptics, gentian violet, methylene blue, brilliant green, and bismuth compounds.

4. The composition according to claim 2, wherein the one or more antimicrobial agents includes a mixture of Iodine and potassium iodide.

5. The composition according to claim 4, wherein the mixture of Iodine and potassium iodide is at a ratio of 1:2.

6. The composition according to claim 1, wherein the device is an endotracheal tube or a tracheostomy tube.

7. A method for removing mucus from a surface of a device inside a trachea, comprising:
    applying a composition of claim 1 to the surface of the device to dissolve the mucus;
    allowing the mucus to dissolve; and
    removing the mucus from the trachea.

8. The method according to claim 7, further comprising one or more antimicrobial agents.

9. The method according to claim 8, wherein the antimicrobial agent is selected from a group consisting of a taurinamide derivative, a phenol, quaternary ammonium surfactant, chlorine-containing, quinoline, quinaldinium, lactone, dye, thiosemicarbazone, quinone, sulfa, carbamates, urea, salicylamide, carbanilide, amide, guanide, amidine, chelate, imidazoline biocides, acetic acid, benzoic acid, sorbic acid, propionic acid, boric acid, dehydroacetic acid, sulfurous acid, vanillic acid, esters of p-hydroxybenzoic acid, ethanol, isopropanol, propylene glycol, benzyl alcohol, chlorobutanol, phenylethyl alcohol, 2-bromo-2-nitropropan-1,3-diol, formaldehyde, glutaraldehyde, calcium hypochlorite, potassium hypochlorite, sodium hypochlorite, iodine (in various solvents), povidone-iodine, hexamethylenetetramine, noxythiolin, 1-(3-choroallyl)-3,5,7-triazo 1-azoniaadamantane chloride, taurolidine, taurultam, EDTA, N(5-nitro-2-furfurylidene)-1-amino-hydantoin, 5-nitro-2-furaldehyde semicarbazone, 3,4,4'-trichlorocarbanilide, 3,4',5-tribromosalicylanilide, salicylanilide, 3-trifluoromethyl-4,4'-dichlorocarbanilide, 8-hydroxyquinoline, 1-cyclopropyl-6-fluoro-1,4-dihydro-4-oxo-7-(1-piperazinyl)-3-quinolinecarboxylic acid, 1,4-dihydro-1-ethyl-6-fluoro-4-oxo-7-(1-piperazinyl)-3-quinolinecarboxylic acid, hydrogen peroxide, peracetic acid, phenol, sodium oxychlorosene, parachlorometaxylenol, 2,4,4'-trichloro-2'-hydroxydiphenol, thymol, benzalkonium chloride, cetylpyridinium chloride, silver, nanosilver, silver sulfadiazine, silver nitrate, 5 fluorouracil, phenolic antiseptics, gentian violet, methylene blue, brilliant green, and bismuth compounds.

10. The method according to claim 8, wherein the one or more antimicrobial agents includes a mixture of Iodine and potassium iodide.

11. The method according to claim 10, wherein the mixture of Iodine and potassium iodide is at a ratio of 1:2.

12. The method according to claim 7, wherein the device is an endotracheal tube or a tracheostomy tube.

13. A method for removing built-up sputum or mucus from a surface of a tracheal cuff tube or in a lumen of a tube inside a trachea of a patient, comprising:
    applying a composition of claim 1 to the surface of the tracheal cuff tube or in the lumen of the tube to dissolve the built-up sputum or mucus;
    allowing the built-up sputum or mucus to dissolve; and
    suctioning the built-up sputum or mucus from the surface.

* * * * *